United States Patent [19]
Gogolewski

[11] Patent Number: 4,770,664
[45] Date of Patent: Sep. 13, 1988

[54] MULTILAYERED PROSTHESIS MATERIAL AND A METHOD OF PRODUCING SAME

[75] Inventor: Sylwester Gogolewski, Renens, Switzerland

[73] Assignee: Mendinvent S.A., Lausanne, Switzerland

[21] Appl. No.: 777,777
[22] PCT Filed: Jan. 17, 1985
[86] PCT No.: PCT/SE85/00018
§ 371 Date: Sep. 13, 1985
§ 102(e) Date: Sep. 13, 1985
[87] PCT Pub. No.: WO85/03444
PCT Pub. Date: Aug. 15, 1985

[30] Foreign Application Priority Data
Feb. 3, 1984 [SE] Sweden ................................ 8400567

[51] Int. Cl.⁴ ............................ A61F 2/06; A61F 2/10
[52] U.S. Cl. .............................................. 623/66; 623/1; 623/12; 623/15; 427/2; 264/41
[58] Field of Search ..................... 623/1, 12, 66, 15; 521/64; 264/41; 523/112, 113, 114; 427/2

[56] References Cited
U.S. PATENT DOCUMENTS

| | | |
|---|---|---|
| 3,526,224 | 9/1970 | Potts . |
| 3,715,326 | 2/1973 | Träubel et al. .................... 521/64 X |
| 3,813,466 | 5/1974 | Anderson . |
| 3,920,588 | 11/1975 | Träubel et al. ........................ 521/64 |
| 4,090,010 | 5/1978 | Warwicker et al. .............. 521/64 X |
| 4,101,984 | 7/1978 | MacGregor ......................... 427/2 X |
| 4,161,948 | 7/1979 | Bichon . |
| 4,173,689 | 11/1979 | Lyman et al. . |
| 4,207,128 | 6/1980 | Träubel et al. .................... 521/64 X |
| 4,265,928 | 5/1981 | Braun .................................. 623/1 X |
| 4,289,125 | 9/1981 | Hung . |
| 4,459,317 | 7/1984 | Lambert ................................. 427/2 |
| 4,548,844 | 10/1985 | Podell et al. ....................... 427/2 X |
| 4,585,666 | 4/1986 | Lambert ................................. 427/2 |
| 4,666,437 | 5/1987 | Lambert ............................. 427/2 X |

FOREIGN PATENT DOCUMENTS
2802295 7/1978 Fed. Rep. of Germany .

Primary Examiner—Richard J. Apley
Assistant Examiner—Alan W. Cannon
Attorney, Agent, or Firm—Burns, Doane, Swecker & Mathis

[57] ABSTRACT

A method producing a multilayered prosthesis material for use with a living body, said material showing mechanical compliance vis-à-vis soft body tissue and possessing biocompatibility. The method comprising the steps:

(a) preparing a copolymer solution using a solvent;
(b) coating a substrate with a uniform thickness of said solution;
(c) precipitating the initial coating resulting from step (b) to form a physically stable structure having pores substantially uniformly distributed therein by treating the coating with a precipitating solution which is miscible in said solvent but functioning as a precipitating non-solvent with respect to the copolymer; and
(d) repeating steps (a)-(c), as required to form the multilayered material, characterized by preparing in step (a) a solution containing less than 5% by weight of polymer. Also disclosed is a multilayered prosthesis material possessing biocompatibility and showing mechanical compliance vis-à-vis soft body tissue, comprising several porous layers of block copolyurethane interconnected by linking fibers integral with the respective adjacent layers.

11 Claims, 1 Drawing Sheet

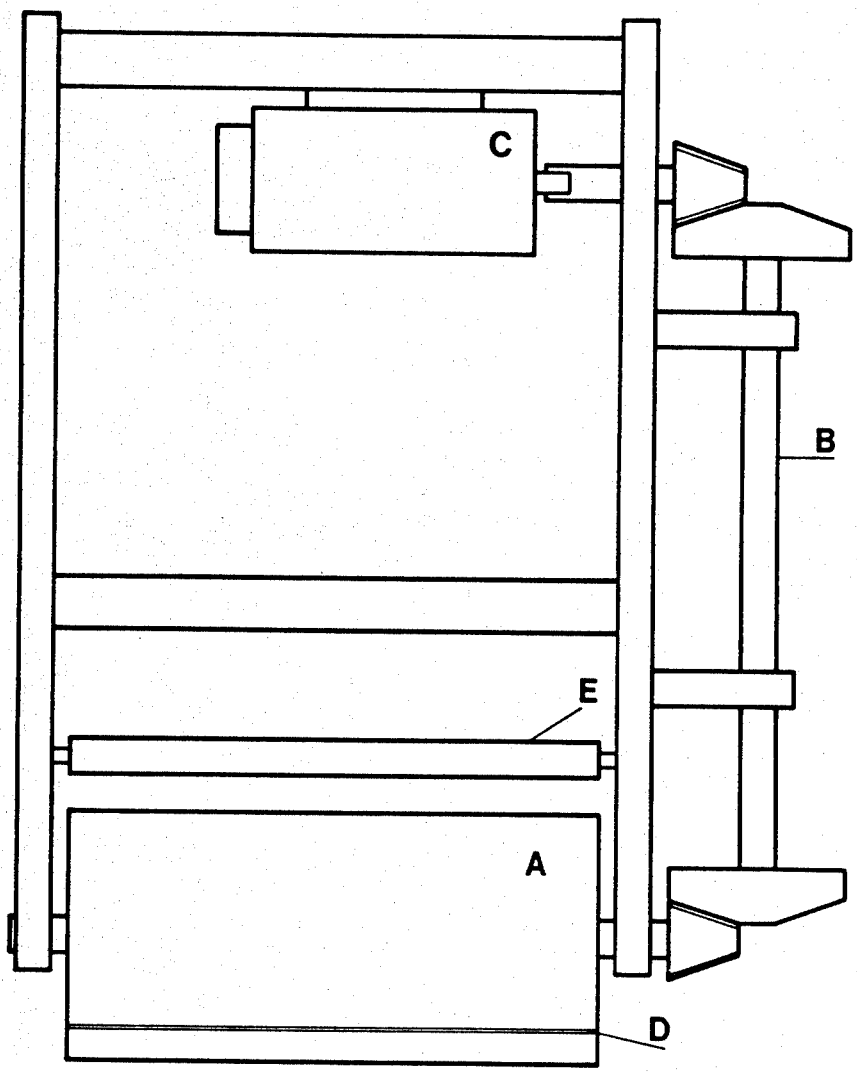

MULTILAYERED PROSTHESIS MATERIAL AND A METHOD OF PRODUCING SAME

The present invention relates to the provision of a multilayered prosthesis material for use with a living body, the material produced showing mechanical compliance vis-à-vis soft body tissue and, furthermore, possessing biocompatibility. The invention also covers a method for the manufacture of such material.

In using synthetic polymers as replacement material for various types of human tissue, it is not only the biocompatibility properties of the polymer which is of critical importance to the performance of the material when used with a living body. In addition to biocompatibility, and blood compatibility the mechanical compliance and porosity features are of basic importance. The available materials are not satisfactory in this respect. In other words, due to mechanical factors the applied material does not possess a mechanical performance which is in line with that of the surrounding natural tissue.

Accordingly, it is an object of the present invention to provide a prosthesis material of a synthetic nature showing mechanical compliance vis-a-vis soft body tissue at the same time possessing biocompatibility or blood compatibility.

Another object of the invention is to provide a multilayered prosthesis material for such use, which shows desirable porosity in combination with mechanical resistance and compliance.

Yet another object of the invention is to provide a method for producing such prosthesis material, the method comprising a new feature of using a solvent of a special nature.

In connection with extensive research and experimentation it has been found that a multilayered prosthesis material can be prepared starting from a solution of a copolymer in a suitable solvent and coating a substrate with a uniform thickness of such solution. It is known from U.S. Pat. No. 4,173,689 to manufacture a replacement material by precipitating a polymer in a concentration of the polymer in solvent between 5-12% by weight. However, at this concentration the viscosity of the polymer solution is relatively high, resulting in thick layers of polymer solution when coating a substrate e.g., a mandrel by dipping. Therefore, only one or few coating-precipitating steps are needed to produce a prosthesis wall, such as a graft, of a desired thickness.

Even if the products made according to above described U.S. patent have a better compliance than, for instance, other synthetic materials used as prosthesis in tissue replacement, they have a spongy texture (column 3, line 29) which doe not give satisfactory tissue compatibility. At the high concentration of polymer used in this prior art method, many of the pores in the polymer matrix are not interconnected. Another disadvantage of this known technique when preparing a multilayered product, is the fact that delamination of the layers after implantation may occur due to the lack of interconnection between same.

According to the present invention it has been surprisingly found that by using a polymer solution containing less than 5% by weight of polymer, a polymer layer, when precipitated, will be obtained which has a fibre-like structure, the pores of which are interconnected. The precipitated fibre-like material consists of fibres of different thickness from tiny fibres to relatively thick ones. Each precipitated layer is very thin and has a thickness of for example about 0.01–0.5 mm and, therefore, usually up to about 100 and even more layers may be applied in subsequent operations to produce a multilayered prosthesis material of a required mechanical strength. Due to the fibre-like porous structure, the prosthesis wall is strong, highly compliant and mechanically compatible with the tissue to be replaced.

It is preferred to use an even more dilute polymer solution such as less than about 3% by weight, and more particularly, less than about 2% by weight of polymer. In some cases, even concentrations as low as about 1% and less may be useful.

After coating the substrate with the polymer solution the coating applied is precipitated by treatment with a precipitating solution which is miscible in the solvent but functions as a precipitating non-solvent with respect to the polymer. This is then repeated as desired to form a multilayered product.

It has been found that the pore size is very much dependent on the concentration of the polymer solution. An example of relationship between pore size and polymer concentration for a specific copolyurethane is given below.

| Concentration % by weight | Average pore size, micron |
| --- | --- |
| 0.20 | 300–500 |
| 1.00 | 100–300 |
| 1.25 | 50–150 |
| 1.45 | 35–60 |
| 2.00 | 30–50 |
| 4.00 | 5–15 |

By using the multilayer precipitating technique according to the invention and described above, it is possible to produce a multilayer prosthesis wall for tissue replacement with different pore size in the different layers. For example in a vascular prosthesis it is possible to produce inner layers e.g. the layers of the lumen of the prosthesis with a relatively small pore size (5–10 microns) to ensure endothelization, but the center and the outer layers are produced with a relatively large pore size (30–100 microns) to ensure a good tissue ingrowth.

In some cases using the multilayered product delamination upon implantation may occur. According to another aspect of this invention such a possible problem can be eliminated in the following manner.

The initial coating resulting from applying the polymer solution on the substrate is precipitated by treating the coating to displace the solvent present in the coating with a precipitating solution which comprises, as a major constituent, a fluid which is miscible with said solvent but functions as a precipitating non-solvent with respect to the polymer, and further comprising, as a minor constituent, a solvent for the polyurethane. This procedure is then repeated the desired number of times to form a multilayered material.

It has been found that if some solvent is left in the precipitated polymer layer, repeating the procedure to form another layer or coating results in the formation of new fibres which form a mechanically strong linkage between the first layer and the subsequent layer. This will prevent progressive delamination of the graft wall when implanted in a living body. Such delamination is a disadvantage associated with the conventional art and generally results in the formation of extensive aneurisms upon implantation.

This strong linkage between the layer may be accomplished either by using a mixed solvent-non-solvent as outlined or by interrupting the treatment with precipitating solution to leave some solvent in the coating when applying the subsequent layer.

Although the invention is not limited to any specific theory or mechanism, there are different factors which might explain how the very strong linkage is achieved. It has been observed that there are many fibres in the boundary of two subsequent layers, which seem to be interlocked probably due to the fact that many tiny fibres in the outer surface of the first layer are partly dissolved in the highly diluted solvent contained in the non-solvent/solvent precipitation liquid system. As soon as new fibres are precipitated in the subsequent precipitation step, the partly dissolved fibres produced in the preceding step are also reformed, thus giving an interlocking effect of the two subsequent layers. There are also fibres precipitated in the second subsequent layer, which are trapped in the pores of the first layer. There may also be a kind of gluing effect between fibres in the outer surface of the first layer and the inner surface of the second layer. This results from the presence of small amounts of solvent left in the precipitated polymer.

In the method of the present invention the polymer used for preparing the solution for coating the substrate can be any polymer useful in the context, but it is preferred to use a copolyurethane, particularly a block copolyurethane. In coating the substrate there is used a solution containing less than 5% by weight of polymer. The lower limit is not critical and may be less than 1% by weight. A particularly preferred range is about 1 to 3%.

The technique of this invention permits easy production of multilayered products with different average pore sizes of the individual layers. This is done by varying the concentration of polymer in the casting solution, i.e., the solution to be applied onto the substrate. This is useful, for example, for the preparation of a vascular prosthesis, where it is desired to have the lumen face of prosthesis with a much lower pore size, such as within the range about 5 to 15 $\mu$m. This is to facilitate epithelization after implantation. On the other hand, it is desired that the remaining part of the prosthesis wall has larger pores to allow faster tissue ingrowth.

As a solvent there may be used any solvent having the ability to dissolve the polymer used. preferred solvents are those selected from the group consisting of tetrahydrofurane, amide solvents and sulfoxide solvents. Among such solvents there may be mentioned in addition to tetrahydrofurane (THF) dimethylacetamide (DMAc), dimethylformamide (DMF) and dimethylsulfoxide. Particularly preferred is a mixed solvent of THF and DMF.

As a non-solvent there may be used any fluid having the capacity to precipitate the polymer. A preferred non-solvent is water but also lower alkanols, such as ethanol, may be used, optionally, in combination with water.

As previously indicated segmented aliphatic polyurethanes or segmented aromatic polyurethanes may be used in applying the technique of this invention. In order to obtain materials which are non-toxic, non-mutagenic and non-carcinogenic, it is preferred to use segmented aliphatic polyurethanes or using another expression, aliphatic block copolymers.

The polymeric material for use in the invention may be conventionally prepared from aliphatic polyurethanes based on diisocyanates, e.g., 1,2-diisocyanatoethane, 1,5-diisocyanato pentane, hexamethylene diisocyanate, methane diisocyanato pentane, 1,9-diisocyanato nonane, 1,8-diisocyanato octane, 1,4-diisocyanato butane, 4,4'-methylenebiscyclohexyl diisocyanate, lysine diisocyanate, 1,4-transcyclohexane diisocyanate, dimethyldiisocyanato silane, diethyldiisocyanato silane. In addition to such diisocyanates there may be used polyols having average molecular weight within the range of 500 to 10000, e.g. poly(ethylene adipate), poly(tetramethylene adipate), poly(1,4-cyclohexyldimethylene adipate), poly(hexamethylene oxalate), poly(hexamethylene glutarate), poly(E-aprolactone), poly(tetramethylene oxide), poly(ethylene oxide), poly(1,2-propylene oxide). Chain extenders, e.g., 1,4-butandiol, 2,4,6-tris(dimethylaminomethyl)-phenol, glycerol, 3,6-dioxaoctane 1–8-diol, ethylene diol, diethylene may also be used diol, tetramethylene diamine, ethylene diamine, hexamethylene diamine, propylene diamine.

The copolyurethanes are conventionally formed by, e.g., reacting a prepolymer such as a polyether diol, with a diisocyanate, and the product, resulting from such reaction may then be chain extended by reacting with a diol or diamine. By such polymerization process, copolymers may be produced having preferred molecular weights and preferred viscosities in solution. By varying the molecular weight and thus the viscosity of the polymer in solution, the rate of degradation and porosity of the material prepared may be controlled.

The selected polymer material is dissolved in a suitable solvent of the type indicated above and the proportions between polymer and solvent are suitably selected so as to give a percentage of solids in the resulting solution of less than 5% by weight. The coating solution is then used to coat a substrate to form an initial coating of uniform thickness. As a substrate there may be used any mechanical means of suitable type, such as a metal plate or a metal mandrel, preferably coated with a resistant plastic, such as polytetrafluoro ethylene. The coating can be provided by spraying, immersion or dipping or in some other conventional manner.

The multilayered prosthesis material of the present invention can be used in a multitude of medicinal applications. Thus, it can be used as a vascular graft, as a skin graft or as a wound dressing. Moreover, it can be used as elastic membranes for ear drum replacement, as elements for orthopedic surgery and as anticoagulant tubing for blood transfusion.

The invention will now be further described by specific examples which, however, must not be construed to limit the scope of the invention. In this connection, reference is also made to the appended drawing, wherein there is shown a casting device for the preparation of a multilayered material in accordance with the present invention.

The casting device shown in the drawing includes a frame carrying a rotary cylinder A. The cylinder may be of sintered glass or its surface may be covered with polytetrafluoroethylene, viz. "FLUON", manufactured by ICI Limited, England. Cylinder A is arranged to be driven by an electric motor C through gears and a gear shaft B. The rotational speed of cylinder A can be easily adjusted for controlling the coating formed on the cylinder. The level of polymer solution is indicated at D.

EXAMPLE I

General Production Procedure

Using the casting device shown in the drawing, the cylinder A is dip-coated at room temperature with a polymer solution. The applied polymer coating is then precipitated with a non-solvent possibly containing a minor amount of solvent. After the first layer of polymer is precipitated, this procedure is repeated for the desired number of cycles to prepare superimposed layers of polymer coatings on the cylinder to produce a multilayered prosthesis material of the required mechanical strength and thickness. After the deposition of the desired number of layers on cylinder A, the material produced is soaked in deionized water to remove all residual solvents and non-solvents, and the material may then be washed with ethanol and dried on the cylinder at, for example, 30° C. in a vacuum oven.

The average thickness of the individual polymer layer is in the range of about 0.01 to 0.2 mm, and the average pore size in the material prepared is in the range about 1 to 500 $\mu$m. For example, using a concentration of polyurethane of about 2% by weight, an average pore size will be obtained lying within the range of about 30 to 50 $\mu$m.

In using the technique of this invention, it is preferred that some solvent is always left in the precipitated polymer coating at the moment when the subsequent polymer coating is deposited on the underlying one.

In practical use the product or material of this invention may, of course, include reinforcing materials, such as materials in porous, woven or pleated form. Such reinforcing material may be degradable or non-degradable.

It is to be noted that the invention is not limited to the casting technique described above, but other methods of applying the polymer solution onto a substrate may be used equally well. Thus, application by spraying is also useful and brushing technique is also conceivable.

EXAMPLE II

Preparation of non-degradable material for medical use

Polyurethane of an average molecular weight of about $4 \times 10^5$ based on 4,4'-methylene-bis cyclohexyl diisocyanate, poly(tetramethylene oxide) and 1,4-butane diol is dissolved in tetrahydrofurane at room temperature and precipitated with water/ethanol (9:1 v/v) mixture. The precipitated polymer is washed with distilled water and dried under vacuum. The dried polymer is then dissolved in dichloromethane to produce a solution having a concentration of polymer of about 2% by weight. The polyurethane is precipitated with n-hexane and dried to constant weight.

Two casting solutions are next prepared by dissolving the purified polymer in tetrahydrofurane at room temperature to form one polymer solution containing about 2% by weight of solids and another containing about 4%.

Using the procedure outlined in Example I, hydrolytically stable vascular prostheses are prepared from the polymer solutions obtained as described above. The wall of the prosthesis is composed of 2+28 layers of precipitated polymer, the layers being intimately and permanently attached to each other through the interface linkages by the small amount solvent remaining in each precipitated layer of polymer. The porosity of the vascular prosthesis material produced lies within the range of about 5–15 $\mu$m for the first two layers using the 4% solution, the remaining layers using the 2% solution lying within about 30–50 $\mu$m. When used as a vascular prosthesis the material shows good endothelization and tissue ingrowth.

EXAMPLE III

Degradable Vascular Prosthesis

A polyester urethane having an average molecular weight of about $9.0 \times 10^4$ prepared from hexamethylene diisocyanate, poly(ethylene adipate)diol and 1,4-butanediol, is dissolved in a mixture of tetrahydrofurane, dimethylformamide and dimethylacetamide (2:1:1 v/v). The concentration of polyurethane in the solution is 2.5% by weight.

Using the procedure described in Example I, a vascular degradable prosthesis is prepared composed of 20 layers of polymer to form a wall thickness of about 1.5 mm and a pore size within the range of about 10–50 $\mu$m.

Using the material as a prosthesis for vascular replacement results in fast endothelization of the lumen and gradual substitution of the prosthesis by living tissue, thus preventing long-term foreign body reactions.

EXAMPLE IV

Degradable wound dressing

A casting solution is prepared from degradable polyesterurethane based on hexamethylene diisocyanate, poly(hexamethylene glutarate)diol and 1,4-butanediol. The polyurethane prepared has an average molecular weight of about $2 \times 10^4$.

Using the polyurethane, a casting solution is formed by dissolving the polyurethane in dimethyl formamide, the concentration of polyurethane being 1.5% by weight.

The procedure of Example I is followed by using a casting device provided with a cylinder made of sintered glass. In the casting procedure, the cylinder is continuously flushed with deionized water. Water penetrates through the pores of the sintered cylinder causing uniform precipitation of the polymer on the surface of the cylinder. Five degradable layers are deposited on the cylinder having an average porosity within the range 35–60 $\mu$m. The polymer membrane on the cylinder is then flushed with ethanol which is subsequently evaporated.

Another casting solution is prepared by dissolving non-degradable Esthane-polyether urethane in tetrahydrofurane at room temperature. The concentration of polymer in the solution is adjusted at 0.9% by weight. The polymer solution is stirred ½ hour before use, filtrated and stored in dark, closed bottles.

Using this second casting solution, another three layers of polymer are deposited on the first five layers on the cylinder. Drying these outer polymer layers leaves a semipermeable membrane having a porosity in the range of 0.5–1 $\mu$m.

The whole composite polymer material deposited on the cylinder is finally washed with ethanol, deionized water and again with ethanol. The material is removed from the cylinder, dried at 30° C. under a vacuum of 20 mbar and placed in polyethylene bags for sterilization. This artificial wound dressing composed of two different membranes connected together is placed with the degradable face on the wound. This degradable layer ensures a proper epithelization and successive tissue ingrowth in the dressing and is finally replaced with newly synthesized stable connective tissue.

The upper layer made from non-degradable polyurethane ensures the proper fluid transport rate, 1 to 4 mg/hr/cm$^2$, and protects the wound against bacterial invasion.

This layer is finally stripped off the rehealed wound.

This artificial skin protects the wound for at least 20 to 60 days without rejection and without requiring an immune supression.

It shows excellent adherence to the wound and high flexibility.

While the invention has been described with reference to certain specific examples using specific materials, solvents, etc., and a specific technique for applying the different layers, it is to be noted that the invention is in no way limited to such specific features since obvious variations and modifications will be apparent to those skilled in the art. Therefore, the invention is not limited otherwise than as is defined by the scope of the appended claims.

What is claimed is:

1. A method of producing a multilayered prosthesis material for use with a living body, said material showing mechanical compliance vis-a-vis soft body tissue and possessing biocompatibility, said method comprising the steps:
   (a) preparing a polymer solution using a solvent wherein said polymer solution contains less than 5% by weight of polymer;
   (b) coating a substrate with a uniform thickness of said solution;
   (c) precipitating the intial coating resulting from step (b) to form a physically stable structure having pores substantially uniformly distributed therein by treating the coating with a precipitating solution which is miscible in said solvent but functioning as a precipitating non-solvent with respect to the polymer; and
   (d) repeating steps (a)-(c), as required, to form a multilayered material.

2. The method of claim 1, wherein the solution prepared in step (a) contains less than about 3% by weight of polymer.

3. The method of claim 1, wherein at least a portion of the solvent is left in each preceding layer when the subsequent layer is applied.

4. The method of claim 3, wherein the precipitating solution comprises as a major constituent, a fluid which is miscible in said solvent but functions as a precipitating non-solvent with respect to the polymer, and further comprises as a minor constituent, a solvent for the polymer, whereby when repeating steps (a)-(c), due to the presence in the precipitating solution of solvent, mechanical binding will be obtained between said initial coating and the subsequent one.

5. The method of claim 3, wherein the treatment of the coating with the precipitating solution is interrupted so that a portion of the solvent is left in the coating when the subsequent layer is applied.

6. A method according to claim 1, wherein said polymer solution contains a copolyurethane.

7. A method according to claim 6, wherein the polymer is a segmented copolyurethane.

8. A method according to claim 1, wherein the solvent is selected from the group consisting of tetrahydrofurane, amide solvents and sulfoxide solvents.

9. A method according to claim 1, wherein the non-solvent is selected from water and lower alkanols.

10. The method of claim 1, wherein by varying the concentration of polymer in the solution of step (a) a multilayered material is produced wherein the different layers have different average pore sizes.

11. The method of claim 2, wherein the solution prepared in step (a) contains less than about 2% by weight of polymer.

* * * * *